(12) United States Patent
Knowles et al.

(10) Patent No.: US 7,541,580 B2
(45) Date of Patent: Jun. 2, 2009

(54) DETECTOR FOR CHARGED PARTICLE BEAM INSTRUMENT

(75) Inventors: William Ralph Knowles, Forest Grove, OR (US); Milos Toth, Cambridge, MA (US)

(73) Assignee: FEI Company, Hillsboro, OR (US)

( * ) Notice: Subject to any disclaimer, the term of this patent is extended or adjusted under 35 U.S.C. 154(b) by 255 days.

(21) Appl. No.: 11/731,743

(22) Filed: Mar. 30, 2007

(65) Prior Publication Data

US 2008/0035861 A1 Feb. 14, 2008

Related U.S. Application Data

(60) Provisional application No. 60/787,847, filed on Mar. 31, 2006.

(51) Int. Cl.
*H01J 37/252* (2006.01)
(52) U.S. Cl. .................................................. 250/310
(58) Field of Classification Search .................. 250/310
See application file for complete search history.

(56) References Cited

U.S. PATENT DOCUMENTS

| 4,249,077 A | 2/1981 | Crawford |
| 4,785,182 A | 11/1988 | Mancuso et al. |

(Continued)

FOREIGN PATENT DOCUMENTS

| JP | 5174768 A | 7/1993 |
| WO | WO 2004/027808 A2 | 4/2004 |

OTHER PUBLICATIONS

Milos Toth and Ralph Knowles "Secondary Electron Imaging of Nonconductors with Nanometer Resolution," 2006 American Institute of Physics, Applied Physics Letter 88, (2006) pp. 023105-023105-3.

B. L. Thiel et al. "Two-Stage Gas Amplifier for Ultrahigh Resolution Low Vacuum Scanning Electron Microscopy," 2006 American Institute of Physics, Review of Scientific Instruments 77 (2006) pp. 033705-033705-7.

Yukinori Ochiai, Jun-Ichi and Shinji Matsui "Electron-Beam-Induced Deposition of Copper Compound with Low Resistivity," J. Vac. Sci. Technol B. 14(6) Nov./Dec. 1996, pp. 3887-3891.

Albert Folch, Jordi Servat, Joan Esteve and Javier Tejada "High-Vacuum Versus "Environmental" Electron Beam Deposition," J. Vac. Sci. Technol. B. 14(4), Jul./Aug. 1995, pp. 2609-2614.

C. K. Crawford "Charge Neutralization Using Very Low Energy Ions," Scanning Electron Microscopy/1979/II, SEM Inc. 99. 31-46.

*Primary Examiner*—Kiet T Nguyen
(74) *Attorney, Agent, or Firm*—Scheinberg & Griner, LLP; Michael O. Scheinberg

(57) ABSTRACT

A detector for use with a high pressure SEM, such as an ESEM® environmental SEM from FEI Company, extends the effective detection space above the PLA, thereby increasing secondary signal amplification without increasing working distance or pressure. Embodiments can therefore provide improved resolution and can operate at lower gas pressures.

31 Claims, 3 Drawing Sheets

U.S. PATENT DOCUMENTS

| | | |
|---|---|---|
| 4,897,545 A | 1/1990 | Danilatos |
| 5,250,808 A * | 10/1993 | Danilatos et al. ............ 250/310 |
| 5,502,306 A | 3/1996 | Meisburger et al. |
| 5,578,821 A | 11/1996 | Meisberger et al. |
| 6,172,363 B1 | 1/2001 | Shinada et al. |
| 6,184,525 B1 | 2/2001 | Van Der Mast |
| 6,329,826 B1 | 12/2001 | Shinada et al. |
| 6,365,896 B1 | 4/2002 | Van Der Mast |
| 6,525,317 B1 | 2/2003 | Yang |
| 6,538,254 B1 | 3/2003 | Tomimatsu et al. |
| 6,590,210 B1 | 7/2003 | Essers |
| 6,972,412 B2 | 12/2005 | Scholtz et al. |
| 6,979,822 B1 * | 12/2005 | Stewart et al. .............. 250/310 |
| 7,241,361 B2 | 7/2007 | Keller et al. |
| 2008/0073534 A1 * | 3/2008 | Katane et al. ............... 250/310 |

\* cited by examiner

DETECTOR FOR CHARGED PARTICLE BEAM INSTRUMENT

This application which claims priority from U.S. Provisional Pat. App. 60/787,847, filed Mar. 31, 2007, which is hereby incorporated by reference.

TECHNICAL FIELD OF THE INVENTION

The present invention relates to electron microscopes.

BACKGROUND OF THE INVENTION

In a scanning electron microscope (SEM), a region of a sample that is to be investigated is probed by a primary beam of electrons that move along an optical axis of the device. The electrons incident on the sample liberate other charged particles from the sample. The energy of these secondary particles, which is substantially lower than the energy of the particles in the primary beam, provides information on the nature, structure and composition of the sample. For this reason, an SEM is often provided with a secondary particle detection apparatus to detect these liberated particles. Conventional SEMs operate in a vacuum to prevent gas molecules from scattering the primary beam and interfering with the collection of secondary particles.

If, for example, the secondary particle detection apparatus is provided with an electrode that is maintained at a positive voltage, secondary electrons liberated from the sample will move toward that electrode. The secondary electrons captured by the electrode produce a current in the detector, which current can be amplified and can provide information about the sample at the impact point of the primary beam. It is possible, therefore, to create an image of the sample by compiling the information obtained from points in an area scanned by the primary beam. It will be apparent that, in connection with the quality of the image thus obtained, particularly the speed with which the image is recorded and the signal-to-noise ratio, it is useful to have the detected current as large as possible.

Electron microscopes that operate with the sample under a relatively high pressure are described for example in U.S. Pat. No. 4,785,182 "Secondary Electron Detector for Use in a Gaseous Atmosphere." Such devices are known as Environmental Scanning Electron Microscopes or a High Pressure Scanning Electron Microscopes (HPSEMs). An HPSEM uses a pressure limiting aperture (PLA) between the relatively high pressure sample chamber and the electron focusing column to maintain a high vacuum in the column. The diameter of the PLA is sufficiently small to prevent rapid diffusion of the gas molecules in the sample chamber into the focusing column, so that the primary beam travel through a high pressure region is limited to its path below the PLA.

In an HPSEM, the sample that is to be investigated is placed in an atmosphere of a gas having a pressure typically between 0.1 Torr (13 Pa) and 50 Torr (7000 Pa), and more typically between 1 Torr (130 Pa) and 10 Torr (1,300 Pa) whereas in a conventional SEM the sample is located typically in a vacuum of about $10^{-6}$ Torr ($1.3 \times 10^{-6}$ mbar). Unlike a conventional SEM, an HPSEM can readily form electron-optical images of moist or non-conducting samples, such as biological samples, plastics, ceramic materials and glass fibers, which would be difficult to image under the typical vacuum conditions of a conventional SEM. The HPSEM allows samples to be maintained in their natural state, without being subjected to the disadvantageous effects of drying, freezing or vacuum coating, which are normally necessary in studies of such samples using conventional SEMs. The gaseous atmosphere of an HPSEM sample chamber provides inherent charge neutralization, that is, the dissipation of surface charge that accumulates on a non-conductive sample as a result of irradiation. Dissipating surface change increases resolving power of the microscope.

The gaseous atmosphere in an HPSEM also makes improved detection means possible. In an HPSEM, the liberated secondary electrons that move in the direction of the secondary electron detector will collide en route with gas molecules in their path. This collision will result in the liberation of new electrons, referred to as "daughter electrons," from the gas molecules. The daughter electrons will also move in the direction of the secondary electron detector. In their turn, these newly liberated daughter electrons will again collide with other gas molecules, and so forth, so that an amplification of the secondary electron signal occurs. The term secondary electron is used to include daughter electrons and reflected primary beam electrons, was well as electrons emitted directly from the sample. The greater the distance that the secondary electrons travel to the secondary electron detector, the greater the number of collisions that will occur between secondary electrons and gas molecules and so the greater the amplification achieved. On the other hand, it is desirable that the primary beam path through the pressurized sample chamber be as short as possible because the gas molecules present scatter the primary beam electrons.

Japanese patent publication 5-174768(A) describes an HPSEM wherein the primary beam from the particle source is focused on the sample by a magnetic immersion lens. The immersion lens consists of a magnetic dipole having poles located on opposite sides of the sample. The magnetic field will cause the secondary electrons liberated from the sample to follow a helical path on their way to the detector. It is claimed that in this way, the distance traversed by the secondary electrons is increased, so that the collision probability increases proportionately and the amplification factor of the detection apparatus increases.

In the configuration described in JP5-174768(A) the electrons follow a helical path around an axis that extends parallel to a magnetic field. The distance traversed by the electron from the sample to the detector is directly dependent upon the distance between the detector and the sample in the direction of the magnetic field. The detector electrode should be therefore be located as high as possible above the sample, so as to achieve as large an amplification factor as possible. Consequently, the distance traversed by the primary beam through the gaseous atmosphere will also be large, and scattering of the primary beam will increase. An increased amplification factor for the detection apparatus is thus achieved at the expense of the resolving power of the illustrated device.

An improved environmental scanning electron microscope is described in U.S. Pat. No. 6,972,412 for "Particle-Optical Device and Detection Means," to Scholtz et al. (Scholtz), which is hereby incorporated by reference and which is assigned to FEI Company, the assignee of the present invention. In the invention of Scholtz, a portion of the detector volume includes an electric field having a component parallel to the magnetic field, and a portion has an electric field having a component perpendicular to the magnetic field. Secondary electrons are subjected to both axial oscillations (i.e., the Penning effect, also referred to as the "yo yo" effect), and radial oscillations (i.e., the "magnetron" effect). These oscillations greatly increase the secondary electron path length, and hence the number of collisions with gas molecules, thereby increasing the amplification of the secondary electron signal. The electric and magnetic fields are such to assure that a significant number of electrons in the detector space have sufficient energy to ionize the gas molecules.

FIG. 1 shows an example of an improved HPSEM 100 using a detector 102 in accordance with the principals of Scholtz. In a sample chamber 104, an electrode assembly 106 is attached to the bottom of pole piece support 108 that supports a pole piece 110 of a lens 112. The electrode assembly 106 includes an anode 120, an ion trap 122, and a pressure limiting aperture electrode 124 having a hole that defines a pressure limiting aperture, PLA 126. Insulating spacers 128 separate the various electrodes. A primary electron beam 134 is directed through PLA 126 toward a sample 136 positioned on a movable sample stage 138. A gas is introduced into sample chamber 104 from a gas source 140. Secondary electrons are emitted from the sample 136 upon impact of the primary beam 134. The secondary electrons are accelerated toward the anode 120, and preferably undergo a combination of magnetron and penning oscillation. The secondary electrons lose energy as they collide with the gas molecules are eventually collected by the anode 120. Ionized gas molecules are collected by the ion trap 122, the sample 136, and the PLA 126. Secondary electrons have the distance, d, available between the sample and the PLA electrode to create additional electrons by collisions with gas molecule. In the detector described by Scholtz, the PLA is flush with the bottom of the pole piece. The secondary electrons therefore have only the distance, $d_2$, available to create additional electrons by collisions with gas molecule. By positioning the PLA inside the lens, the improved configuration provides additional detector space in which the gas can be ionized to amplify the secondary electron signal, without increasing the working distance, that is, the distance between the lens and the sample. Although positioning the PLA inside the lens provides additional detector space, there are still some disadvantages to the embodiment shown in FIG. 1.

1. The height of the active part of the detector volume, while extended compared to the original Scholtz configuration, is still limited by the distance "d" between the sample and the PLA, thereby limiting the detector space.

2. Because the sample chamber is maintained at a relatively high pressure to provide adequate amplification, the PLA diameter must be relatively small to maintain a sufficient vacuum in the electron beam column. The small diameter restricts the deflection of the primary beam, thereby restricting the field of view of the HPSEM in some applications.

3. While the detector geometry shown in FIG. 1 is useful, for example, in an electron column in which the pole pieces have a 4 mm bore, it is difficult to accommodate an in-lens PLA within pole pieces having a 2 mm bore. Consequently, for lenses having small bores, the PLA is positioned flush with the bottom of the lens, instead of inside the lens, and the height of the detection space is reduced to $d_2$. This decrease must then be compensated for by an increase in working distance, that is, the distance between the lens and the work piece, the gas pressure, or both, at the expense of resolution and beam scatter in the gas. Also, the configuration shown in FIG. 1 is more difficult to implement in systems optimized for coincident electron and ion beams.

4. If the height of the yo yo oscillation about the anode described by Scholtz causes secondary electrons to travel beyond the PLA, those secondary electrons will often be collected by an electrode above the PLA (the electron trajectories being determined by the geometry and intensity of the electric and magnetic fields inside the electron optical column). Consequently, said electrons will not be available to participate further in the amplification process or to be collected by the anode as part of the detection current. Similarly, if the height of the yo yo oscillation about the anode described by Scholtz causes secondary electrons to contact the PLA, those secondary electrons will not be available to participate further in the amplification process or to be collected by the anode as part of the detection current. Electrons can hit the bottom of the PLA while traveling upward from the sample or the top of the PLA on the return path back into the detector volume. The magnitude of the yo yo oscillation is determined by the electron energy loss rate to the gas during the oscillatory motion. Thus, for adequate amplification, the system should be configured to provide a high probability that secondary electrons will lose enough energy through collisions with gas molecules so that they do not reach the PLA on the first oscillation. The probability of collisions increases with the gas pressure and with the distance between the sample and the PLA. The minimum usable chamber pressure, P, is therefore limited by d. For a secondary electron to avoid being lost to the column and to avoid collection by the PLA during the first half-cycle of the yoyo, the electron must lose to the gas an amount of energy, $\Delta E$, that is greater than or equal to its initial emission energy. The magnitude of $\Delta E$ increases with the product of P times d. In some embodiments of the present invention, d is increased beyond the PLA by making the PLA diameter sufficiently large to prevent the collection of secondary electrons traveling past the PLA electrode, and the electric field above the PLA is configured to prevent the loss of secondary electrons to the column.

5. The height of the yo yo oscillation described by Scholtz can be limited by applying a negative bias to the PLA. In such a configuration, however, a secondary electron emitted from the sample will return to impact the sample after the first full cycle of the yoyo if the amount of energy, $\Delta E$, lost to the gas during the first full cycle of the yoyo is smaller than the initial secondary electron emission energy. That is, the amplification space can be effectively doubled, but that increase is still too small to prevent the loss of a significant fraction of secondary electrons to the sample under conditions of low pressure and short working distance. This is particularly true when the pole piece bore diameter is too small to implement an "in-lens" PLA such as that shown in FIG. 1.

6. During typical operation of a charged particle beam, the beam is "blanked," that is, directed into a solid obstruction to the side of the column optical axis, when it is desired that the beam should not impact the work piece. When the beam is unblanked, that is, when the beam is re-directed to the sample, the beam tends to drift for a short period of time. Applicants have found that this drift is caused by the accumulation of charge on the PLA electrode, possibly on the native oxide or on any contamination layers that may be present and may create a thin insulating layer. The drift magnitude varies inversely with PLA diameter. Because of the relatively high gas pressures required to provide sufficient amplification, detector 102 typically requires a PLA having a relatively small diameter to maintain a low pressure in the focusing column and the small diameter PLA results in greater drift magnitude.

SUMMARY OF THE INVENTION

An object of the invention is to provide improved gas amplification at lower sample chamber pressures for charged particle beam instruments This invention extends the active part of the detector volume beyond the pressure limiting aperture, thereby increases the detector volume without increases the distance between the lens and the sample.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more through understanding of the present invention, and advantages thereof, reference is now made to the following descriptions taken in conjunction with the accompanying drawings, in which.

DETAILED DESCRIPTION OF PREFERRED EMBODIMENTS

Embodiments of the present invention increases the active detector space by extending the space available for electron motion through the PLA and into the pole piece, thereby increasing the effective detector space without increasing the working distance. Detector performance limitations imposed by the distance between the sample and the PLA are therefore eliminated. Because the detector space can be larger than the working distance, it is not necessary to have a large working distance to provide a sufficient detector space, and embodiments of the invention therefore permit a column design having a shorter working distance which improves resolution.

Figure 1:
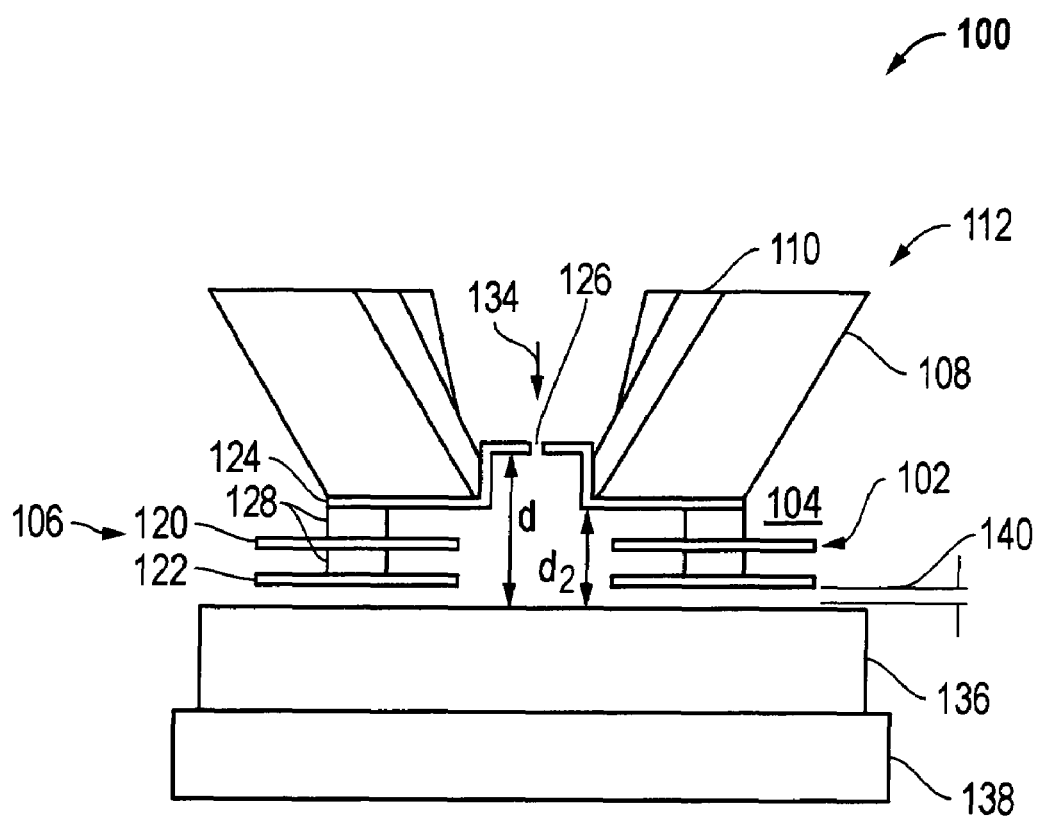
FIG. 1 shows an embodiment of the system described in Scholtz et al.

By increasing the efficiency of the gas amplification, embodiments of the invention permit operation at reduced pressures. In some embodiments of the present invention, the PLA diameter is increased compared to a typical PLA diameter of a prior art system, which allows more secondary electrons to pass through the PLA. An electrode above the PLA helps shape an electric field that directs secondary electrons above the PLA back toward the sample, where the gas pressure is greater and those electrons are then available to participate in further amplification and to be collected by the anode. The improved amplification efficiency permits the system to operate at lower pressure, which allows the use of a larger diameter PLA Embodiments of the present invention can provide superior amplification in a system in which the final lens bore is too small to permit the use of a PLA that extends into the lens, as shown in FIG. 1.

Figure 2:
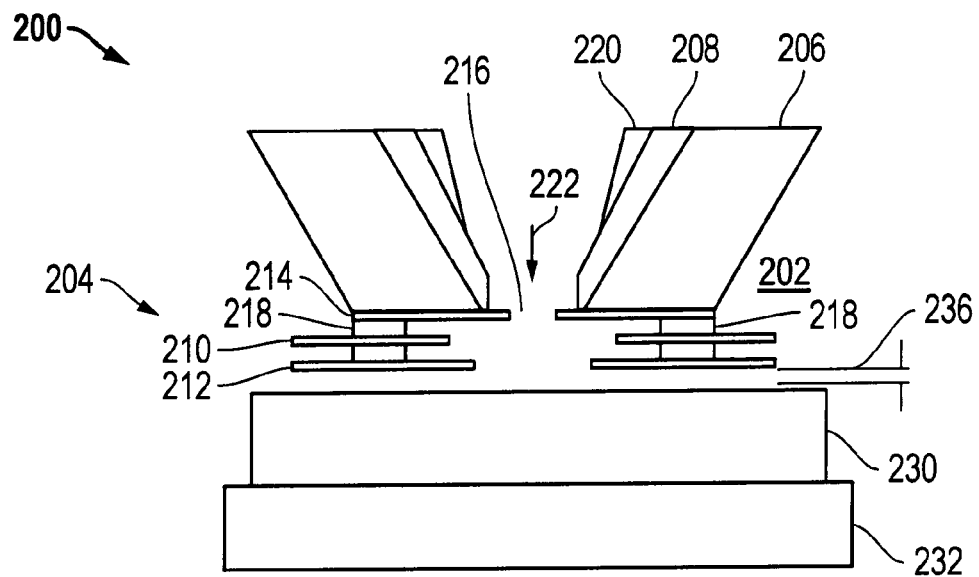
FIG. 2 shows a first embodiment of the invention.

FIG. 2 shows a preferred embodiment of the invention. In a preferred HPSEM 200 having a sample chamber 202, an electrode assembly 204 is attached to the bottom of a pole piece support 206 that is attached to the pole piece 208 or the roof of the specimen chamber (not shown). The electrode assembly 204 includes an anode 210, an ion trap 212, and a PLA electrode 214 having a hole that defines a PLA 216, the electrodes separated by insulating spacer 218. An electrode 220 is positioned above the PLA 216 and is electrically isolated (not shown) from the pole piece 208. A primary electron beam 222 is directed through PLA 216 toward a sample 230 positioned on a movable sample stage 232. A gas is introduced into sample chamber 202 from a gas source 236. Secondary electrons are emitted from the sample 230 upon impact of the primary beam 222. The secondary electrons are accelerated toward the anode 210, and under the combination of electric and magnetic fields preferably undergo motion as described in Scholtz, that is, a combination of magnetron and Penning oscillation. The secondary electrons lose energy as they collide with the gas molecules and are eventually collected by the anode 210. Ionized gas molecules are collected by the ion trap 212, the sample 230 and the PLA electrode 214.

The electrode 220 provides a significant electric field above the PLA and in the lens interior. PLA 216 has a diameter, unlike the prior art, that is sufficiently large to allow electrons to oscillate though the PLA and back. That is, the electrons can travel into the lens and then back to undergo collisions to create more free electrons, and eventually be collected by the anode. Some collisions will also occur above the PLA, as the larger PLA produces a more gradual pressure drop off.

Figure 3:
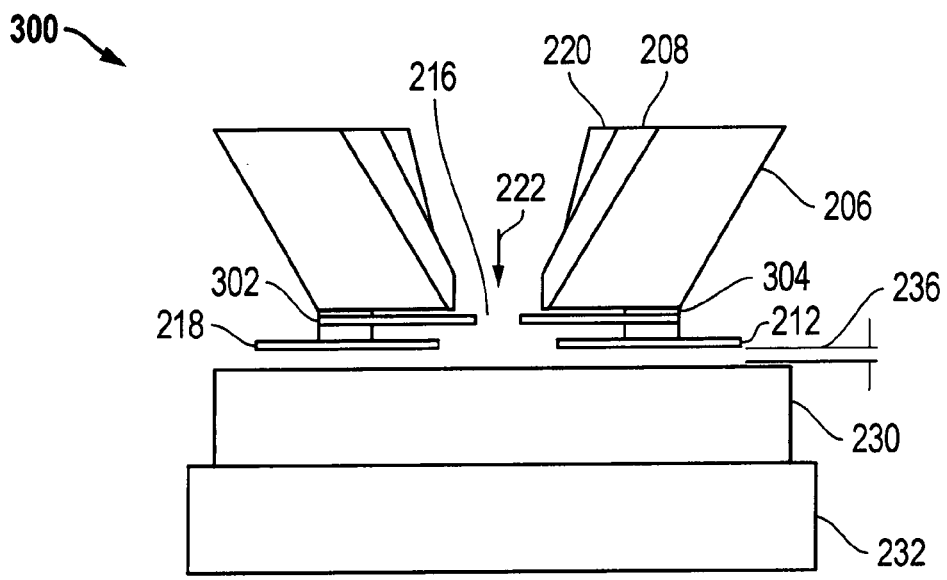
FIG. 3 shows a second embodiment of the invention.

The invention is not limited to any particular arrangement of electrodes. For example, the PLA electrode 214 may be electrically isolated from the pole piece 208 and may be biased in order to tailor the electric field below and above the PLA 216. For example, FIG. 3 shows an embodiment of an HPSEM 300 that is similar to the embodiment of FIG. 2, but in which the functions of anode and PLA are served by a single electrode 302 separated from the pole piece 208 and pole piece support 206 by an insulating spacer 304.

Figure 4:
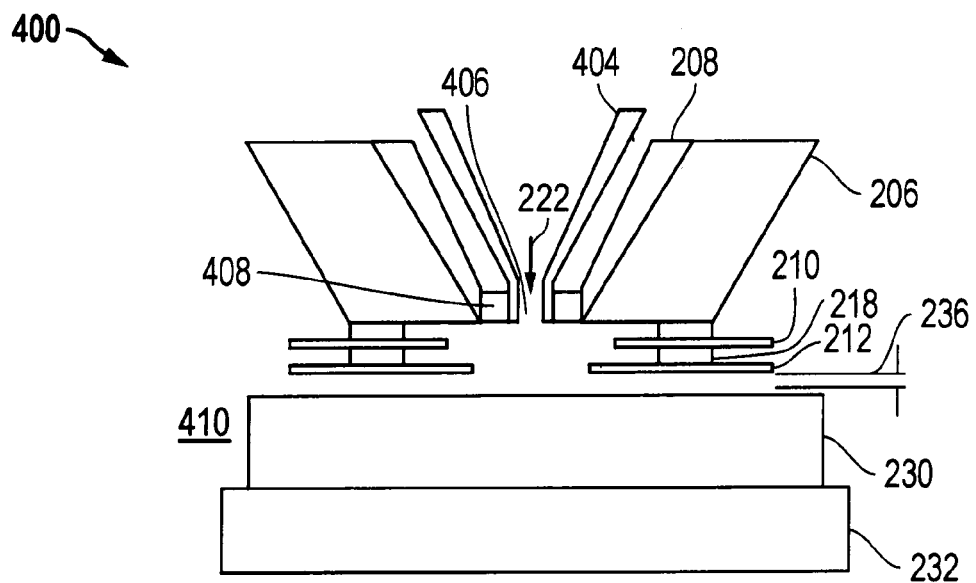
FIG. 4 shows a third embodiment of the invention.

FIG. 4 shows an embodiment of an HPSEM 400 in which an electrode 404, positioned within the pole piece 208, provides an electric field within the lens and also serves to define a pressure limiting aperture 406. Electrode 404 is connected to a power supply (not shown) and is electrically isolated from pole piece 208 by insulating spacers 408. Electrode 404 restricts gas flow from the chamber 410 into the column. This can be achieved by making the inner diameter of electrode 404 sufficiently small (e.g., less than 2 mm), and optionally, by shaping 402 so as to minimize gas conductivity, such as by making the base of the electrode tubular, as shown in FIG. 4.

In preferred embodiments, the PLA radius is preferably sufficiently large to prevent substantial secondary electron collection by the PLA electrode. The minimum PLA radius must be greater than the maximum radial distance between the centre of the PLA and the position of secondary electrons passing through the PLA. On a typical, properly aligned system, at a given pressure, this distance is determined by:

a. The maximum Larmor radius of secondary electrons passing through the PLA. As described in Scholtz, the motion of the electrons in the electric and magnetic fields can be described as a superposition of a few simpler motions, including a circular motion having a radius referred to as the Larmor radius; and b. The geometry of the magnetic and electric fields above the PLA. These fields determine the maximum possible radial displacement of secondary electrons above the PLA. The magnetic field geometry is particularly significant in the case of columns in which it decays rapidly with axial distance beyond the pole tip.

The diameter of the PLA is typically larger than that of a prior art system. Because the increased detector volume allows for increased gas amplification at a given pressure, the detector can operate at lower pressures than can prior art systems. Hence, any increase in gas pressure inside the electron beam column caused by the increased PLA diameter can be offset by decreasing the pressure inside the specimen chamber.

Typical component sizes and operating parameters are provided below. Skilled persons will be able to determine suitable operating parameters for embodiments suitable for different application. As described in Scholtz, it is preferred to size the components, such as the anode, in relation to the voltages and magnetic field strength, to produce electric and magnetic fields that provide both the magnetron and the Penning effect for maximum application. The values provided below are merely examples, and are meant to provide guidance to skilled persons in finding suitable parameters for different applications. Embodiments may fall outside of these suggested ranges, which are not intended to be limitations on the scope of the invention. In particular, the functionality of the electrodes is determined by potential differences between the electrodes. Hence, electrode biases can be offset by any arbitrary amount, so as to produce equivalent potential differences, without deviating from the scope of the invention.

A PLA preferably has a diameter of preferably between 0.1 mm to about 4 mm, with the most preferred diameter being about 1 mm. The anode and ion trap typically each has a diameter of between about 0.1 mm and about 10 mm, with a preferred diameter of about 3 mm.

The PLA is preferably electrically isolated from the pole piece and maintained at a potential of between about −1000 V to about 2000 V, with ground potential being a typical potential. The anode is preferably biased within a range of about 0 volts to about 2000 volts, with a potential of about 400 V being the most preferred. The ion trap is preferably biased within a range of about −1000 volts to about 2000 volts, with ground potential being the most preferred. The sample stage is preferably biased within a range of about −1000 volts to about 1000 volts, with a ground potential being the most preferred.

Because embodiments of the invention provide for more efficient application, the system can operate at a lower pressure, which in turn facilitates the use of a larger PLA without compromising the electron beam. Embodiments typically operate at a pressures of between about a millitorr (0.13 Pa) and a Torr (133 Pa), with a pressure of about 0.1 Torr (13 Pa) preferred. A typical magnetic field strength of the lens is about 0.1 Tesla. Lower field strengths can be used (e.g., 0.01 Tesla), but result in reduced secondary electron confinement efficiency, and reduced gas gain in most configurations. Greater field strengths can be used, but are difficult to realize in practice. Because the detector volume is increased, the detector can operate at lower gas pressures. For example, the chamber pressure ranges from about 1 Torr (133 Pa) to about 10 mTorr (0.13 Pa). The lower pressure allows use of a larger diameter PLA without fouling the electron source or scattering the electron beam. Imaging can be performed using any of the signals, such as electrons, ions or photons, generated in the gas cascade.

Figure 5:
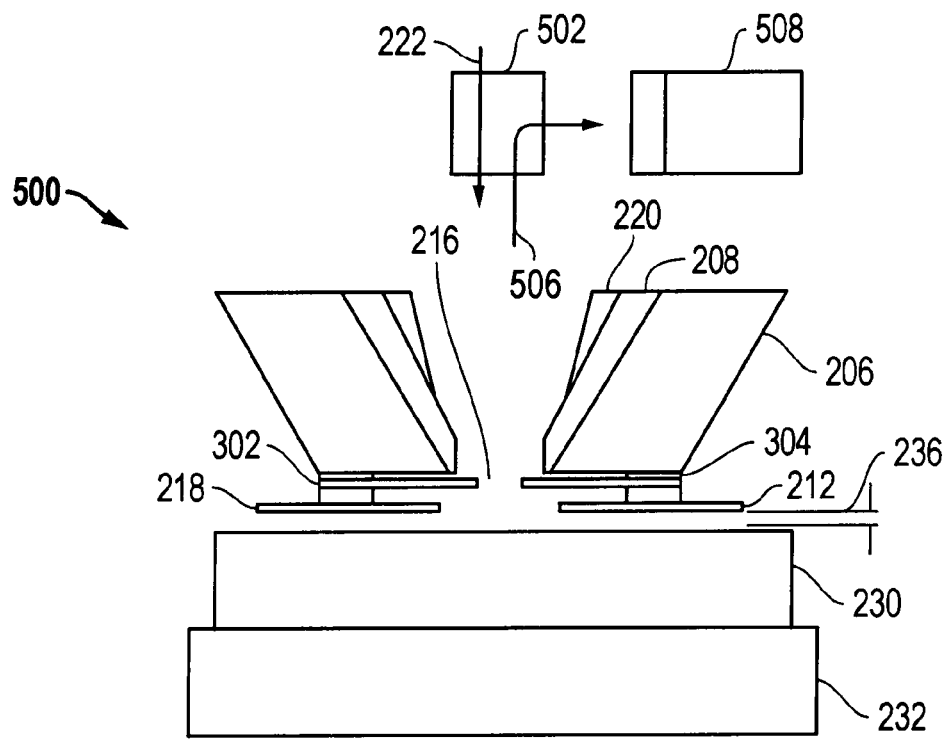
FIG. 5 shows a fourth embodiment of the invention.

Alternatively, as shown in FIG. 5, an electron microscope system 500 can use a conventional, high vacuum through-the-lens (TTL) detector positioned above the PLA for imaging, while an electrode assembly structure position in the sample chamber is used for charge control. FIG. 5 shows a deflector 502, such as a Wien filter, that passes the primary electron beam 222 toward the sample, while deflecting secondary electrons 506 to a detector 508, such as a scintillator-photomultiplier tube.

Through-the-lens detection and charge control are achieved by:

a. Making the gas pressure and PLA diameter sufficiently small to prevent gas breakdown at TLD electrodes; and.

b. Biasing the TLD suction tube and deflection electrodes such that some fraction of secondary electrons are collected by the TLD, while the remainder are gas amplified within a structure such as that shown in FIG. 3. The gas amplification generates ions for charge control. The fraction of ions incident onto the sample surface is controlled by the ion trap geometry and bias.

As described above, incidental insulating layers on a PLA tend to accumulate charge, and the accumulated charge causes the primary beam to drift when the beam is unblanked. In a preferred embodiment, the PLA is constructed of a material that will minimize charge accumulation. For example, the PLA can be constructed from a metal that has a relatively conductive oxide. An example of a metal with a "conductive" oxide is molybdenum. Native oxides conduct once a certain critical voltage is applied across them. In the case of molybdenum, this voltage is low and so any beam drift caused by charging up of the oxide is also low. Another example of a PLA that is constructed of a material that will minimize charge accumulation is a PLA coated with carbon, or a PLA made of graphite.

The use of a material having a "conductive oxide" is known and used in some applications, such as electron column and spectrometer design. HPSEMs, however, are known to reduce sample changing because of the positive and negative charged particles in the detection space, so it was unexpected that the PLA would charge, and that the charging would cause a problem in the operation of the instrument.

In prior art detectors, the gas gain decreases rapidly with decreasing pressure at pressures lower than about 0.3 Torr (40 Pa). This decrease in gain is caused by collection of secondary electrons by the PLA electrode, and can account for a loss of over 90% of the imaging signal. That is, at a sufficiently low pressure, over 90% of the electrons can be collected by the PLA electrode. For example, at 0.1 Torr (13 Pa), more than 50% of the electrons can be collected by the PLA electrode. Embodiments of the present invention can reduce this figure to below 5%, and gas gain becomes limited by other factors.

Thus, in preferred embodiments of the present invention, when dropping pressure from 0.3 Torr to 0.1 Torr (40 Pa to 13 Pa), the secondary electron signal gain is decreased by less than 50%, more preferably by less than 25%, even more preferably by less than 10%, and most preferably by less than 5%. The percentage of electrons collected by the PLA is roughly proportional to the decrease in signal. In some embodiments, when dropping pressure from 0.3 Torr to 0.1 Torr (40 Pa to 13 Pa), a significant number of electrons, preferably more than 15%, more preferably more than 25% and most preferably more than 50%, of the secondary electrons that pass through the PLA and return at least once to below the PLA. Thus, in preferred embodiments, the diameter of the PLA is sufficiently large and the electric field above the PLA is sufficiently strong such that the signal loss is reduced to the levels described above in this paragraph.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A particle-optical apparatus, comprising:
    a sample holder arranged in a sample chamber for receiving a sample;
    a particle source arranged for producing a primary beam of first electrically charged particles along an optical axis for irradiating said sample;
    a pressure limiting aperture having a diameter, the pressure limiting aperture maintaining the pressure in the sample chamber at a higher pressure than the pressure in an electron optical column;
    a first electrode having an aperture and arranged for detecting electron signals originating from the sample due to said irradiation;
    a detection space formed above said sample holder and extending above the pressure limiting aperture;
    a magnetic lens for providing a magnetic field for focusing the primary beam in the vicinity of the sample holder;
    wherein the detector space includes an electric potential field that has a saddle point inside the detector space, the corresponding electric field causing electrons to oscillate about the saddle point, at least one of the electron oscillations bringing the electrons above the pressure limiting aperture to improve the detection efficiency.

2. The apparatus of claim 1 in which the pressure limiting aperture has a radius greater than the maximum Larmor radius of secondary electrons passing through the pressure limiting aperture.

3. The apparatus of claim 1 in which the pressure limiting aperture has a radius greater than one millimeter.

4. The apparatus of claim 1 in which the pressure limiting aperture has a radius greater than the maximum radial displacement of a substantial number of secondary electrons above the pressure limiting aperture.

5. The apparatus of claim 1 in which the pressure limiting aperture is tubular and extends into the electron column.

6. The apparatus of claim 1 in which a pole piece of an electron column restricts gas flow from the sample chamber, thereby acting as the pressure limiting aperture.

7. The apparatus of claim 1 in which the pressure limiting aperture has a diameter sufficiently large to allow sufficient electric field from the first electrode to extend above the pressure limiting aperture to maintain the electron oscillation about the saddle point.

8. The apparatus of claim 1 in which the pressure limiting aperture has a diameter greater than twice the Larmor radius of the electrons.

9. The apparatus of claim 1 in which the first electrode and an immersion lens are arranged for providing an electric field and a magnetic field such that the detection space comprises a portion in which the electric field includes a component ("E") that is oriented transverse to the magnetic field ("B") and in which $2*m*(E/B)^2/q$ is greater than the ionization energy of a gas, where "m" is the mass of an electron and "q" is the charge of an electron, the apparatus operating in an amplification domain that provides magnetron enhanced amplification of an electron signal from the sample.

10. The apparatus of claim 1 in which the magnetic lens comprises an immersion lens and in which the active part of the detector volume is extended beyond the pressure limiting aperture, into a pole piece.

11. The apparatus of claim 1 in which the pressure in the sample chamber is maintained at a pressure sufficiently great to provide gas amplification of a secondary electrons and sufficiently small to prevent contamination of the particle source.

12. The apparatus of claim 11 in which the pressure in the sample chamber is maintained at a pressure of less than about 1 Torr (133 Pa).

13. The apparatus of claim 12 in which the pressure in the sample chamber is maintained at a pressure of between about 1 Torr (133 Pa) and about 10 mTorr (1.3 Pa).

14. The apparatus of claim 1 further comprising a second electrode positioned above the pressure limiting aperture, the second electrode maintained at a voltage to increase the number of electrons that pass through the pressure limiting aperture during the second cycle of an oscillation.

15. The apparatus of claim 14 in which the second electrode is negatively biased relative to the pressure limiting aperture.

16. The apparatus of claim 14 in which:
    a high vacuum detector is positioned above the pressure limiting aperture; and
    the second electrode is biased to provide a secondary electron signal to the high vacuum detector.

17. The apparatus of 16 in which the first electrode is biased to provide charged particles to the sample to neutralize accumulated charge.

18. The apparatus of claim 14 in which a portion of the electrons in the detector space are detected above the pressure limiting aperture and a portion of ions in the detector space are used for charge neutralization.

19. The apparatus of claim 18 in which the ions used for charge neutralization impinge on the sample to neutralize a negative charge.

20. The apparatus of claim 14 in which when dropping pressure from 0.3 Torr to 0.1 Torr, the secondary electron signal gain is decreased by less than 50%.

21. The apparatus of claim 14 in which when dropping pressure from 0.3 Torr to 0.1 Torr, the secondary electron signal gain is decreased by less than 25%.

22. The apparatus of claim 14 in which when dropping pressure from 0.3 Torr to 0.1 Torr, the secondary electron signal gain is decreased by less than 10%.

23. The apparatus of claim 14 in which when dropping pressure from 0.3 Torr to 0.1 Torr, the secondary electron signal gain is decreased by less than less than 5%.

24. The apparatus of claim 14 in which the second electrode above the pressure limiting aperture is maintained at an electrical potential of at least 40 Volts lower than the pressure limiting aperture potential.

25. A method of operating a charged particle beam system, comprising:
    providing an electron source, the electron source being maintained in an electron source volume for maintaining the environment around the electron source at a first pressure;
    providing a sample chamber for holding a sample, the sample chamber being maintained at a second pressure;
    providing a pressure limiting aperture between the source volume and the sample chamber to maintain the pressure difference between the source volume and the sample chamber;

providing a magnetic lens for focusing a beam of electrons originating from the electron source;

directing a beam of electrons from the electron source towards a sample and through the magnetic lens;

accelerating secondary electrons emitted from the sample, the electrons colliding with a gas to produce additional electrons; and providing a magnetic field and an electric field to increase the path of the electrons to increase the number of collisions within a detector space and the number of electrons collected, the electric field extending above the pressure limiting aperture so that the path of a significant number of electrons extends above the pressure limiting aperture, thereby increasing the number of electron collisions with gas molecules and the secondary electron signal.

26. The method of claim 25 in which providing an electric field includes providing an electric potential field that has a saddle point inside a detector space, the corresponding electric field causing electrons to oscillate about the saddle point, at least one of the oscillations of a significant number of electrons bringing those electrons above the pressure limiting aperture to measurably improve the detection efficiency.

27. The method of claim 25 in which providing a magnetic lens includes providing an immersion lens that provides the magnetic field in said detection space, the electric field and the magnetic field provided such that the detection space comprises at least a portion wherein a component ("E") of the electric field is oriented transverse to the magnetic field ("B") and wherein $2*m*(E/B)^2/q$ is greater than the ionization energy of the gas, where "m" is the mass of an electron and "q" is the charge of an electron, the apparatus operating in an amplification domain that provides magnetron enhanced amplification of an electron signal from the sample and in which the detection space extends above a pressure limiting aperture.

28. The method of claim 25 in which providing an electric field includes providing an electrical potential on an electrode above the pressure limiting aperture.

29. The method of claim 25 in which providing a pressure limiting aperture between the source volume and the sample volume includes providing a pressure limiting aperture having a radius greater than the maximum Larmor radius of secondary electrons passing through the pressure limiting aperture.

30. The method of claim 25 in which providing a magnetic field and an electric field to increase the path of the electrons includes maintaining an electrode above the pressure limiting aperture at a voltage to increase the number of electrons that pass through the pressure limiting aperture during the second cycle of an oscillation.

31. The method of claim 25 in which providing a pressure limiting aperture includes providing a pressure limiting aperture having a diameter sufficiently large to allow sufficient electric field from a first electrode to extend above the pressure limiting aperture to maintain the electron oscillations about a saddle point.

* * * * *